United States Patent [19]
Heikkilä et al.

[11] Patent Number: 6,146,856
[45] Date of Patent: Nov. 14, 2000

[54] PROCESS FOR THE PRODUCTION OF ISOMATULOSE AND OTHER PRODUCTS

[75] Inventors: Heikki Heikkilä, Espoo; Marja-Leena Sarkki, Kantvik; Mirja Lindroos, Kirkkonummi; Päivi Ojala, Kantvik; Vili Ravanko, Espoo; Matti Tylli, Kantvik, all of Finland

[73] Assignee: Xyrofin Oy, Kotka, Finland

[21] Appl. No.: 09/082,555

[22] Filed: May 21, 1998

[51] Int. Cl.⁷ .................................................. C12P 19/12
[52] U.S. Cl. .............................. 435/100; 435/72; 435/98; 435/99; 536/123.13; 536/124; 536/127
[58] Field of Search ................................ 435/100, 72, 99, 435/98; 536/123.13, 124, 127

[56] References Cited

U.S. PATENT DOCUMENTS

| | | |
|---|---|---|
| 3,214,293 | 10/1965 | Mountfort . |
| 4,386,158 | 5/1983 | Shimizu et al. . |
| 4,640,894 | 2/1987 | Munir . |
| 4,788,145 | 11/1988 | Munir . |
| 4,857,461 | 8/1989 | Egerer et al. . |
| 5,127,957 | 7/1992 | Heikkila ................................... 127/47 |
| 5,578,339 | 11/1996 | Kunz et al. . |

FOREIGN PATENT DOCUMENTS

| | | |
|---|---|---|
| 1 110 189 | 10/1981 | Canada . |
| 1 185 551 | 3/1983 | Canada . |
| 1 179 283 | 12/1984 | Canada . |
| 0 028 900 | 5/1981 | European Pat. Off. . |
| 0 054 544 | 1/1985 | European Pat. Off. . |
| 0 160 253 | 4/1985 | European Pat. Off. . |
| 0 077 971 | 12/1987 | European Pat. Off. . |
| 0 483 755 A2 | 10/1991 | European Pat. Off. . |
| 0 345 511 B1 | 8/1995 | European Pat. Off. . |
| 1 049 800 | 1/1959 | Germany . |
| 1 448 524 | 12/1974 | Germany . |
| 81-52918 | 4/1981 | Japan . |
| 83-115899 | 10/1985 | Japan . |
| WO97/44478 | 11/1997 | WIPO . |

OTHER PUBLICATIONS

Munir R.M. et al., "1–O—D–Glucopyranosyl–D–Fructose:Production from Saccharose and its Reduction to 1–O—D–Glucopyranosyl–D–Glucitol", pp. 477–485, 1987, Carbohydrate Research, vol. 164.

Saska, M. et al., "Applications of Continuous Chromatographic Separation in the Sugar Industry" III. Desugarization of Cane Molasses:, pp. 403–410, Int. Sugar Jnl, vol. 96, 1150 (1994).

*Primary Examiner*—Francisco Prats
*Attorney, Agent, or Firm*—Scully, Scott, Murphy & Presser

[57] ABSTRACT

The present invention relates to a process for the simultaneous production of converted and non-converted sugar and/or non-sugar products. The process is especially adapted to the simultaneous production of isomaltulose and/or trehalulose, and betaine or invert sugar from plant derived juices. Sucrose in said juices are enzymatically converted into isomaltulose and trehalulose and the target products are separately recovered from the resulting solution. The isomaltulose may be further converted into isomalt.

24 Claims, 1 Drawing Sheet

PROCESS FOR THE PRODUCTION OF ISOMATULOSE AND OTHER PRODUCTS

The present invention relates to a process for the simultaneous obtaining of converted and non-converted sugar and/or non-sugar products. The invention relates especially to the simultaneous production of isomaltulose and/or trehalulose, and betaine or invert sugar.

Isomaltulose (or palatinose) is a reducing disaccharide produced from sucrose. Isomaltulose has been proposed for use as a sweetener in the food industry and it is a raw material for the production of the sweetener isomalt (palatinit) by hydrogenation. Isomalt is a substantially equimolar mixture of α-D-glucopyranosyl-(1,6)-sorbitol and α-D-glucopyranosyl-(1,1)-mannitol.

Trehalulose is another reducing sugar which may be obtained from sucrose. Hydrogenation of trehalulose yields a mixture of α-D-glucopyranosyl-(1,1)-sorbitol and α-D-glucopyranosyl-(1,1)-mannitol also having a sweet taste.

Various processes for the isomerization or transglucosylation of sucrose to isomaltulose and/or trehalulose have been reported. The isomerization is performed by a transglucosylase enzyme which has been found to exist in microorganisms such as *Protaminobacter rubrum, Serratica plymuthica, Erwinia rhapontici, Pseudomonas mesoacidophile*, etc. The known isomerization techniques include isomerization with viable or dead microorganism cells or with the enzyme in extracted form. The enzyme has been used in both immobilized and free form.

Prior art processes for the production of isomaltulose and/or trehalulose are described, for instance, in publications such as EP 028 900, U.S. Pat. No. 4,386,158, U.S. Pat. No. 4,640,894, DE 1 049 800, EP 1 099, EP 77 971, EP 049 801, EP 200 069, EP 160 253, EP 483 755 and EP 625 578. A discussion on the transglucosylation of sucrose is disclosed in the publication Munir, M. et al. Carbohydrate Res. 164 (1987) 477–485. A background art process for the enzymatic production of isomaltulose from molasses is mentioned in the present applicant's co-pending FI application 962095 filed on May 17, 1996. The disclosures of said patents, patent applications and publication are herewith incorporated by reference.

Betaine is a quaternary ammonium compound having the formula $(CH_3)_3N^+.CH_2.COO^-$. It is known to accumulate in sugar beets and it is generally recovered from beet molasses or vinasse by various techniques such as ion exchange, crystallization, extraction or by chromatography. Betaine is used in animal fodder as well as in pharmaceutical and cosmetic applications.

Prior art processes for the recovery of betaine are disclosed, for instance in EP 54 544 and EP 345 511, the disclosures of which are hereby incorporated by reference.

Sugar cane juices do not contain betaine but they provide instead significant amounts of invert sugar, which is a mixture of glucose and fructose. The invert sugar may be used as a sweetener as such or, after purification, it may be separated further into glucose and fructose.

Prior art processes for the obtaining of invert sugar from sugar cane are disclosed, for instance, in the publications Saska, M. et al., Int. Sugar Jnl, 1994, Vol. 96, No. 1150, p. 403–410, and Hongisto, H. et al., Desugarization of cane molasses by the Finnsugar chromatographic separation process, Finnish Sugar Co. Ltd., Kantvik, Finland, Mar. 4, 1977, the disclosures of which are hereby incorporated by reference. Said prior art discusses batch or continuous chromatographic desugarisation of sugarcane molasses. The processes allow separate recovery of sucrose and invert sugar.

Further, U.S. Pat. No. 3,214,293 describes the separation of non-sugars from sugars in an aqueous sugar solution by a combination of ion exchange and ion exclusion.

GB Patent 1 448 524 discloses a method for separating sugars from the non-sugars of beet or cane molasses by liquid distribution chromatography on cation exchangers. Fractions of sugars and non-sugars, including invert sugar and betaine may be recovered.

None of the prior art processes provide for the recovery of betaine or invert sugar in connection with the production of isomaltulose.

An object of the present invention is to provide a process for obtaining valuable sugar and non-sugar products from aqueous plant derived solutions.

Another object of the invention is to provide a new process for producing sugar and non-sugar products from molasses.

A special object of the invention is to provide a process which makes it possible to recover betaine or invert sugar as well as isomaltulose and/or trehalulose from aqueous sugar-containing solutions, especially from molasses.

A further object of the invention is to provide a process for obtaining the hydrogenation products of isomaltulose and/or trehalulose.

It has now been discovered that it is possible to convert the sucrose of aqueous sugar beet or cane derived solutions into isomaltulose and/or trehalulose without materially affecting the betaine or invert sugar, respectively, present in the solution and that the separate target products may be recovered from the resulting liquid in good yields. It has also been discovered that the sugar in molasses may readily be converted into isomaltulose and/or trehalulose and that the produced disaccharide may be effectively recovered while allowing recovery of betaine or invert sugar from said converted molasses.

The present invention is based on the above finding. Accordingly, the present invention provides a process for the simultaneous obtaining of isomaltulose and other sugar and/or non-sugar products, said process comprising the following steps in combination:

a) providing an aqueous plant derived solution containing sucrose as well as target sugar or non-sugar compounds;

b) subjecting said sucrose in said solution to transglucosylation; and c) recovering from said transglucosylated solution isomaltulose and said target sugar and/or non-sugar products.

According to the preferred embodiment of the invention the recovery comprises chromatographic recovery of the target products as separate fractions.

When the plant derived solution contains large amounts of sucrose, such as is the case for thin or thick juices, the process according to the invention may include a step for crystallizing sucrose from the plant derived solution to provide molasses. Alternatively, all the sucrose in said plant derived solution may be used for conversion into isomaltulose and/or trehalulose. When the ratio of isomaltulose in said solution is large, it may be preferable to separate at least a portion of the isomaltulose by crystallization prior to the recovery of the other products.

In a preferred embodiment of the invention the plant derived solution as such comprises molasses. In case the plant derived solution is derived from sugar beets, isomaltulose, trehalulose and betaine are the main target products recovered in step c) of the process. If said solution derives from sugar canes, isomaltulose, trehalulose and invert sugar are recovered in step c).

In another embodiment according to the invention betaine is separated from the solution prior to the transglucosylation of the sucrose.

The conversion of sucrose into isomaltulose and/or trehalulose is preferably provided by a transglycosylating enzyme (sucrose-6 glucosyl mutase) found in micro organisms capable of converting sucrose into isomaltulose and/or trehalulose. The preferred microorganism for the production of isomaltulose is *Protaminobacter rubrum* (CBS 574.77) but also other converting microorganisms may be used. It is also possible to use any of the prior art types of processes with immobilized or free microbial cells or with the enzyme isolated from the cells. In fact, it is necessary only to have the converting activity of the enzyme, and the way in which this enzyme activity is provided is not critical for the performance of the present invention. For instance, enhanced activity may be provided by recombinant techniques.

The sucrose-containing aqueous plant derived solution which forms the raw material for the present process may be a plant juice such as thin or thick juice of a sugar beet or cane mill. On the other hand the thick juice may be used in a conventional way for the production of sucrose by crystallization in one or several crystallization steps to provide molasses, which in turn is suitable as said plant derived solution.

In the context of the present invention the term "plant derived solution" should be understood to encompass any solutions which contain a significant amount of sucrose and other plant derived compounds and which are suitable as raw materials to the present process.

Molasses is the preferred raw material for the present invention since it is easily available in large amounts, it is cheap and its residual contents of sucrose provides a good source for the production of isomaltulose. Molasses contains sucrose and other nutrients such as proteins and minerals which may be utilized for the growth of microbes. Since these nutritive compounds may be used by the microorganisms to sustain their growth, it is possible to maintain a simultaneous growth of converting microorganisms and conversion of sucrose according to the present invention.

Beet molasses contains about 50–70% on dry solids (DS) of sucrose and about 3–8% on DS of betaine and some other nitrogen-containing compounds. Cane sugar molasses contains about 35–55% on DS of sucrose and about 10–35% on DS of invert sugar. Molasses has been mentioned in the prior art as a nutrient for the growth of microorganisms in preparation of cell suspensions for the conversion of sucrose into isomaltulose. However, the actual production of isomaltulose has been performed on pure sucrose solutions or on thick or thin plant juices. Molasses acts as a good nutrient medium for the said bacteria and it has now been found that molasses provides a suitable sucrose source for the actual production of isomaltulose and/or trehalulose. It has also been found that the betaine or invert sugar, respectively, present in the molasses remains materially unchanged in the conversion process and that betaine or, alternatively, invert sugar can be recovered from the resulting reaction mixture separately from the isomaltulose and other sugars and non-sugars.

An advantage of the present invention lies in the fact that since the sucrose of molasses can be used for conversion it will be possible to use existing molasses chromatographic separation mills for the production of both an isomaltulose and a betaine or invert sugar fraction.

BRIEF DESCRIPTION OF THE DRAWING

The invention will now be described in greater detail with reference to the appended drawing, wherein.

Figure 1:
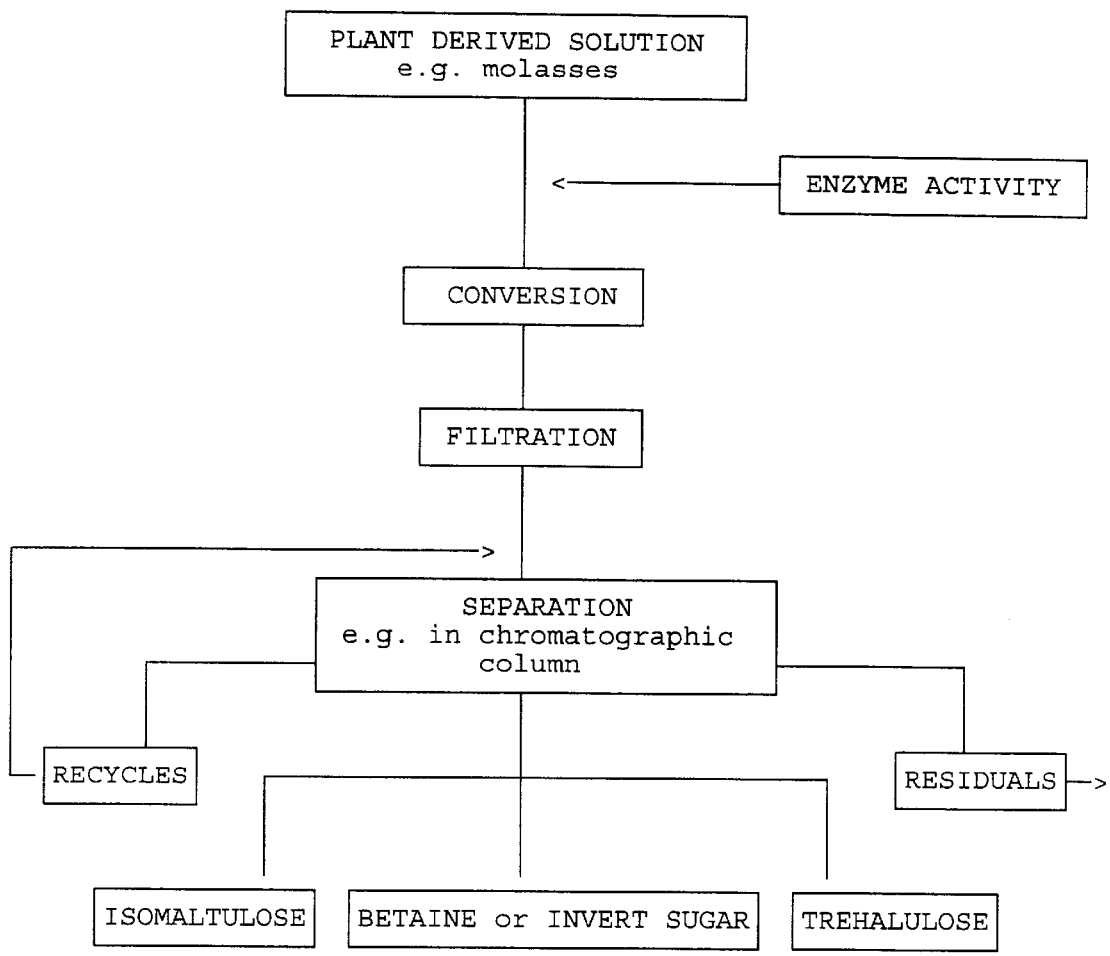
FIG. 1 shows a block diagram of one process according to the invention.

In the following detailed description molasses will generally be used as a raw material for the process of the present invention because of the special benefits deriving from the use of molasses. However, it is evident that also other plant derived solutions may be used for the transglucosylation of the sucrose contained therein and that isomaltulose and the other sugar and/or non-sugar products may be separated from the resulting liquid in the similar way as described for molasses.

Sugar-containing solutions are generally provided by processing sugar containing plants such as sugar beets or sugar cane in a conventional way to provide thin juice. The thin juice may be used as such, after purification, for conversion of the sucrose therein into isomaltulose and/or trehalulose or it may be processed to thick juice. The thick juice may correspondingly be subjected to crystallization to recover most of the sucrose. The crystallization may be a three step crystallization, as is conventional, or one may prefer to crystallize sucrose only once or twice in order to leave more of the sugar in the solution.

According to the invention the sugar containing solution is contacted with a transglucosylating enzyme activity capable of converting the sucrose into isomaltulose and/or trehalulose. In the preferred process the growth medium for a cell suspension of the converting microorganism, such as the production of *P. rubrum* (CBS 574.77), is molasses or a mixture of molasses, corn steep liquor and inorganic nutrients, such as $(NH_4)_2HPO_4$. A fermentation at about 30° C. and pH 7 with good aeration will provide a desired count of microbial cells of $10^9$/ml or more. In batch processes the fermentation broth is added to the sugar containing solution and conversion is performed under suitable converting conditions.

As is well known in the art, it is also possible to immobilize the microorganism cells, dead or alive, in or on a carrier. Alternatively the enzyme may be extracted from the microbial cells and used as such or in an immobilized form to perform the conversion. Reference is made, for instance, to the publications mentioned in the introductory portion of the specification, all of which are included herein by reference.

The process of transglucosylating the sucrose may be performed as a batch-wise or a continuous process in a tank or a column including the enzyme system in an immobilized or non-immobilized form. The batch process may be performed as a fed-batch process, wherein an additional carbon source is fed into the solution to assist microbial growth during conversion. The conversion is preferably carried out at an optimal temperature of 25 to 35° C., preferably about 30° C. with proper aeration. When molasses is used for the conversion anti-foaming agents should preferably be added to the liquid in order to stop excessive foaming.

If the conversion process is performed as a continuous process in a column packed with a carrier having the enzyme immobilized thereon, there may be several columns which may be connected in series and/or in parallel, for instance for allowing one column to undergo regeneration while the other ones are in operation. The solution may also be recirculated through one or several columns to increase the conversion yield.

It is generally preferred to continue the transglucosylation for a sufficient time to convert up to 80% or more of the sucrose. After conversion the solution contains isomaltulose as the main reaction product, and generally some trehalulose, fructose and glucose, as well as any unreacted sucrose in addition to the betaine or, alternatively, invert sugar and other non-converted components of the initial feed solution.

When the desired conversion has been reached any viable microorganism cells should be killed. This may be done, for instance, by raising the temperature to about 80° C. for 30 minutes or more. The dead cells and any other solid residues should be removed by centrifugation and/or filtration prior to subjecting the solution to a chromatographic separation.

In case the conversion is performed on a solution from which sucrose has not been crystallized, the amount of isomaltulose may be so great that it may be preferred to crystallize the main portion of isomaltulose from the solution in a conventional way prior to performing the chromatographic separation.

The chromatographic separation of isomaltulose/ trehalulose and betaine or invert sugar may be performed with the same type of process and equipment as that used in the prior art for separating sucrose and betaine or invert sugar, respectively.

Any insoluble impurities should be removed from the converted solution e.g. by filtration and thereafter softened by ion exchange to remove divalent ions. Thereafter the solution is fed into a chromatographic separation column containing a cation exchange resin in the monovalent form, e.g. Na, K.

In a typical process according to the present invention, the transglucosylated solution is subjected to pasteurization followed by centrifugation and/or filtration to remove any microbial cells. In the case of cane molasses it may be necessary to combine the filtration step with a phosphate precipitation and centrifugation step in order to get a clear solution. The filtered solution is softened e.g. by ion exchange and evaporated to reduce its volume. The filtered solution (preferably at pH 5.5 or higher) is fed into a separation column and eluted with water to provide different fractions of sugar and non-sugar products. The actual composition of the fractions will depend on the initial feed solution used. The separate fractions are generally evaporated again to increase the concentration for the next process steps.

According to the present process the fractions include isomaltulose, some trehalulose, and betaine or invert sugar, respectively. A portion of the fractions may be recycled in order to provide purer products. The isomaltulose obtained in the separation may be crystallized to provide crystalline isomaltulose. The isomaltulose may be used to provide isomalt, which is a commercially used sweetener. Isomalt is produced from isomaltulose by hydrogenation either after crystallization of the isomaltulose or directly from the isomaltulose fraction from the chromatographic column. The hydrogenation of trehalulose also provides a sweetening mixture and the isomaltulose and trehalulose may be combined for hydrogenation. Ion exchange can be used for purification before hydrogenation. Betaine may likewise be recovered from its solution, for instance, as described in EP 54 544 or EP 345 511, incorporated herein by reference. The invert sugar fraction is retained in its liquid form or evaporated to provide a syrup. E.g. ion exchange can be used for further purification of invert sugar before evaporation.

The following Examples illustrate the present invention without, however, limiting it in any way.

EXAMPLE 1

Molasses and Sucrose as a Feed Stock for Isomaltulose/Trehalulose Production

Production of *Protaminobacter rubrum* (CBS 574.77) Fermentation Broth

Stock cultures of *P. rubrum* were maintained on nutrient agar slopes at +4° C. Cells from a culture were diluted with 2 ml of saline. 0.4–0.6 ml of aliquots of the resultant suspension were used to inoculate 9×300 ml aliquots of growth medium in 500 ml sterilized, baffled shake flasks. The inoculated flasks were shaken at 230 rpm at 30° C. for 1 days. The growth medium contained 5% sucrose, 1% peptone, 0.5% yeast extract, 0.3 % beef extract, in 0.01 M $Na_2HPO_4$ buffer at pH 7. When the concentration of $10 \times 10^9$ cells/ml was reached the fermentation broth was used for the transglucosylation in two separate experiments, one from beet molasses and the other from a pure sucrose solution.

Transglucosylation

Beet molasses (Cultor Ltd) containing sucrose 60.7% on DS was used for the molasses test. 2600 ml of the *P. rubrum* growth medium described above was transferred to a conversion fermenter (Biostat, 10 l ) with 7 liters of sterile molasses-water solution. At the beginning of the conversion the sucrose concentration was 200 g/l, the total dry solids concentration 325 g/l and pH was adjusted to pH 7. The conversion was continued for 13 hours in sterile conditions at 30° C., aerating 10 l/min and agitating 350 rpm until almost all sucrose was converted.

When molasses was used in the conversion the foaming was a considerable problem. A continuous detection of foaming and adding of an antifoamer was necessary. When the conversion was completed and no sucrose was detected the conversion was stopped by killing the microbes by arising the temperature of the solution to 80° C. for 30 minutes. The cells and other solid residues were filtered with a Seizt pressure filter using 0.1% Kenite 300 as a body feed.

In a separate experiment a pure sucrose solution was converted in the same conditions as the beet molasses but in the concentration 325 g/l of sucrose.

The compositions of both converted solutions were analyzed by HPLC (ion exchange resin in $Pb^{2+}$-form) and the results are shown in the Table below.

TABLE 1

Transglucosylation of molasses sucrose and pure sucrose

|  | Molasses sucrose | Pure sucrose |
| --- | --- | --- |
| *P. rubrum* fermentation broth dosage counts $(\times 10^9)$/ml | 2 | 2 |
| Isomaltulose yield from sucrose, % | | |
| after 20 h conv. | 73.4 | 82.6 |
| after 47 h conv. | 76.5 | |
| Composition of sugar fraction, % | | |
| isomaltulose | 81.9 | 85.9 |
| trehalulose | 10 | 8 |
| fructose | 3.9 | 3.1 |
| glucose | 2.2 | 2 |
| sucrose | 1.0 | 0 |
| oligosacc. | 1 | 1 |

EXAMPLE 2

Transglucosylation of Molasses Sucrose by *P. rubrum* Cells

Fermentation

Cells from an agar slant of the *Protaminobacter rubrum* strain (CBS 574.77) were diluted with 2 ml of saline. 0.4–0.6 ml aliquots of the resultant suspension were used to inoculate 300 ml of a growth medium in 500 ml sterilized, baffled shake flasks. The inoculated flasks were shaken at 230 rpm at 30° C. for one day. The growth medium contained 60 g/l sucrose, 10 g/l peptone, 6 g/l beef extract in 0.01 M $KH_2PO_4$ buffer at pH 7. 1200 ml of the 1 day old growth medium was transferred to a fermenter (Biostat, 10 l) with 8,5 liters of nutritive medium (sucrose 70 g/l, corn steep liquor 40 g/l, $(NH_4)_2HPO_4$ 0.9 g/l, pH 7).

The fermentation was continued at a temperature of 30° C., at pH 6–7, mixing at 350 rpm, and an aeration rate of 12 l/min, until the cell density had increased up to the $10 \times 10^9$ counts/ml. The whole fermentation broth was used as an inoculum for 1100 liters of the sterile nutrient medium of the above composition in a 1500 l fermenter. The fermentation was performed at 30° C. at an aeration rate of 1100 l/min and a stirring rate 350 rpm.

When a concentration of $10–20 \times 10^9$ cells/ml had been reached, the whole fermentation broth was used for the transglucosylation of sucrose in molasses into isomaltulose and other sugar products.

Transglucosylation

Beet molasses (Cultor Ltd) (1800 kg DS) containing 60% of sucrose on DS was diluted to a concentration of 370 g DS/l, sterilized at 120° C. for 20 minutes, cooled to 30° C. in a reactor vessel (10 m$^3$). The pH was adjusted to pH 6 with $H_2SO_4$. 1100 liters of *P. rubrum* fermentation broth ($10–20 \times 10^9$ cells/ml) was introduced to the beet molasses solution (4800 kg) and allowed to act on sucrose at 30° C. while introducing air at 1500 l/min and mixing at 200 rpm. An antifoaming agent Mazu 100 (PPG Industries Inc. UK) was used to prevent heavy foaming during the conversion. Within 25 hours practically the entire quantity of sucrose in molasses was converted and the sugar composition of the converted solution was the following:

| isomaltulose | 82% on sugars | 49% on DS |
| trehalulose | 8.8% on sugars | 5.3% on DS |
| fructose | 3.3% on sugars | 2% on DS |
| glucose | 2% on sugars | 1% on DS |
| oligosacch. | 3.9% on sugars | 2% on DS |

After the conversion, the *P. rubrum* cell mass was separated from the solution via a separator and the bacteria milk was re-used for a fresh conversion reaction. The solution from the separator was pasteurized at 80° C. for 30 minutes to kill the rest of bacteria. The cooled solution was filtered.

EXAMPLE 3

Chromatographic Separation of Isomaltulose, Trehalulose and Betaine

The transglucosylated solution of Example 2 was subjected to a chromatographic separation in a chromatographic separation column.

The separation was performed in a pilot chromatographic separation column as a batch process. The whole equipment consisted of a feed tank, a feed pump, a heat exchanger, the column, an output pump, product containers, pipelines for input and output of feed solution and eluent water and device and valves for the control of the outcoming liquid.

The column with a diameter of 1.0 m was filled with a cation exchange resin (manufactured by Finex Oy, Finland); the height of the resin bed was about 5.3 m. The cross-linkage degree of the resin was 5.5% DVB and the average particle size about 0.35 mm. The resin was regenerated into sodium ($Na^+$) form and a feeding device was then adjusted to the top of the resin bed. The temperature of the column and feed solution and eluent water was approximately 80° C. The flow rate in the column was adjusted to 630 l/h.

The first pretreatment step of the feed solution was filtration, which was done with a pressure filter using diatomaceous earth as filter aid (temperature of the solution about 80° C.), concentration about 30 g dry substance in 100 g solution). After this, the solution was softened by ion exchange in order to remove calcium ions (temperature about 55° C., concentration the same as in filtration). The solution was then filtered again before the separation.

The chromatographic separation was carried out as follows:

Step 1: The dry substance content of the feed solution was determined and adjusted to 30 g dry substance in 100 g solution (if necessary) according to the refractive index (RI) of the solution Step 2: 120 kg dry substance (DS) of feed solution was pumped through the heat exchanger to the top of the resin bed (through the feeding device).

Step 3: The feed solution was eluted downwards in the column by feeding ion exchanged water to the top of the column (again through the heat exchanger).

Step 4: The density and conductivity of the outcoming solution was measured and monitored by a recorder; according to this information, the outcoming solution was collected and divided into six fractions in the following order; residual fraction number one (containing salts), recycle fraction number one (containing a small amount of salts and isomaltulose), isomaltulose fraction, recycle fraction number two (containing a small amount of isomaltulose and trehalulose), residual fraction number two (containing e.g. glucose and fructose), and betaine fraction.

The amount of dry substance and isomaltulose, betaine and trehalulose content of the feed solution and product fractions are presented in Table 2. The concentrations of the components are expressed as percentages of the total dry substance in the fraction. The yield of isomaltulose, betaine and trehalulose in the product fractions are also presented (the amount of the component in the particular fraction in relation to the total amount of that component in all outcoming fractions).

TABLE 2

| | Compositions and yields | | |
| --- | --- | --- | --- |
| | Feed solution | Isomaltulose fraction | Betaine fraction |
| DS in fraction, kg | 120 | 54 | 12 |
| DS content g/100 g solution | 29.5 | 17.7 | 4 |
| isomaltulose, % on DS | 45.2 | 73 | 4 |
| trehalulose, % on DS | 4.2 | 8.9 | 0.7 |
| betaine, % on DS | 5.7 | 0 | 55 |

TABLE 2-continued

Compositions and yields

|  | Feed solution | Isomaltulose fraction | Betaine fraction |
|---|---|---|---|
| isomaltulose, yield % |  | 95.8 | 1.2 |
| trehalulose, yield % |  | 95.3 | 1.7 |
| betaine, yield % |  | 0 | 94.2 |

Following separations were performed in the same way. The recycle fractions were then also separated, and trehalulose, which was concentrated to some extent in the recycle fraction number two, was collected as a separate fraction just after the isomaltulose fraction. Trehalulose content of this fraction was about 30% on DS.

EXAMPLE 4

Chromatographic Separation of Isomaltulose and Trehalulose

Trehalulose was concentrated to some extent in the latter recycle fraction (the fraction between the isomaltulose and the second residual fraction) of Example 3. The trehalulose fractions were combined, evaporated and separated again in order to separate more isomaltulose and also trehalulose.

This separation was performed similarly as in Example 3 by using the same equipment. However, the linear flow rate was now 0,5 m/h and feed size about 160 kg DS; otherwise, separation conditions were the same as in Example 3. The isomaltulose fraction was collected in the same way as earlier, and the trehalulose fraction then just after the isomaltulose fraction. The yield of product components and the composition of feed and product fractions are presented in Table 3.

TABLE 3

The yield of product components and composition of feed and product fractions

|  | feed solution | isomaltulose fraction | trehalulose fraction |
|---|---|---|---|
| DS in fraction, kg | 160 | 85 | 25 |
| DS content g/100 g solution | 31.6 | 22.1 | 20.6 |
| isomaltulose, % on DS | 45.7 | 62.8 | 37.8 |
| trehalulose, % on DS | 16.1 | 18.2 | 31.1 |
| isomaltulose, yield % |  | 73 | 12.9 |
| trehalulose, yield % |  | 60.1 | 30.2 |

EXAMPLE 5

Crystallization of Isomaltulose

The isomaltulose fractions from the chromatographic separations of Example 3 were subjected to crystallization. The volume of the syrup was 600 l and the DS content about 42%. Part of the feed syrup was concentrated in a 400 l boiling crystallizer to DS content 77.6 g/100 g. The mass (volume about 150 l) was seeded with 147 g of dry, crystalline, milled isomaltulose of an earlier crystallization test. Evaporative crystallization was continued for about 2 hours until the whole feed syrup was used. The DS content of the mass was kept about on the same level during the crystallization.

Before seeding, the temperature and the pressure were, respectively, between 62–65° C. and 190–170 mbar. After seeding, respectively, between 65–67° C. and 160–150 mbar.

After the evaporative crystallization the mass volume was about 300 l. The mass was dropped into a 400 liter cooling crystallizer. A linear cooling program from 67.5 to 30° C. in 41 h was set. After about 27 hours the program was stopped and constant temperature 41° C. was set. 1 liter of water was mixed into the mass. After 16 hours mixing the centrifugings were began. Centrifuging of the mass was done with a Heine Zentrifuge at 2100 rpm for 5 min. The crystals were washed with water.

Results of the centrifuging test are shown in Table 4.

TABLE 4

Crystallization of Isomaltulose

| Mass into the centrifuge (g) | 11650 |
|---|---|
| Washing (ml) | 1190 |
| DS, mass (w-%) | 82.2 |
| Q, mass (% on DS) | 68.0 |
| Crystal cake (g) | 5000 |
| DS, cake (w-%) | 94.7 |
| Q, cake | 99.4 |
| Q, run-off (% on DS) | 38.6 |
| Centrifugation DS yield, (w-%) | 49 | where: Q is the isomaltulose purity (g isomaltulose/100 g DS)

The mass was centrifuged and the crystals were dried in a rotary drum dryer (60° C.). Sieve analysis of the dried crystals gave the average crystal size 200 μm (st. deviation 24%).

Analysis results of the samples are shown in the Table 5.

TABLE 5

Crystallization of isomaltulose

| Sample name[1] | DS[2] g/100 g | ICUMSA colour[3] | Carbohydrate analysis[4] % on DS | | | |
|---|---|---|---|---|---|---|
|  |  |  | Oligo | Isom. | Gluc. | Treh. |
| Seeding | 77.9 | 12100 | 5.7 | 69.2 | 1.5 | 11.7 |
| Start cooling | 82.0 | 12800 | 6.6 | 69.5 | 1.3 | 11.9 |
| End | 82.2 | 16200 | 5.1 | 68.0 | 1.6 | 11.7 |
| Cake | 94.7 | 290 |  | 98.0 | 1.5 | 0.4 |
| Run-off | 60.3 | 34500 | 12.7 | 38.6 | 1.4 | 21.9 |
| Dried cakes | 95.2 | 310 |  | 98.2 | 1.2 | 0.4 |

[1]Explanation of Sample names:
Seeding     sample of the mass just before seeding
Start cooling  sample of the mass at the start of cooling
End         sample of the mass at the start of centrifuging
Cake        sample of the crystal cake of the centrifuging
Run-off     sample of the run-off of the centrifuging
Dried cakes the combined dried cakes
[2]DS = dry substance by the Karl Fischer method
[3]ICUMSA colour = the colour analyzed by adapting the ICUMSA method at pH 5 and measuring the filtered solution (0.45 μm membrane) at 420 nm.
[4]The carbohydrates were analyzed by HPLC by using $Pb^{+2}$ form ion exchange column
Oligo = oligosaccharides
Isom. = isomaltulose
Gluc. = glucose
Treh. = trehalulose

EXAMPLE 6

Hydrogenation of Isomaltulose

Isomaltulose from the isomaltulose fractions of the chromatographic separations of Example 3 were subjected to ion exchange and hydrogenation to provide glycopyranosyl mannitol and glucopyranosyl sorbitol.

For the ion exchange the following resins were used in the disclosed order:

1. a strongly acidic cation exchange resin (Dow 88) in H⁺ form
2. a weakly basic anion exchange resin (Dow 66) in OH⁻ form
3. an adsorbent resin (Dowex Optipore) regenerated with NaOH.

In the ion exchange procedure the amount of resin in each respective column was 0.2 liters. The flow rate was 1.0 l/h and the temperature of the solution was 40° C. A total of 0.5 kg of dry substance was treated in one cycle.

The ion exchanged disaccharide was hydrogenated in a batch type high pressure autoclave (Medimex) provided with a mixer and having a volume of 5 liters. The hydrogenation pressure was 40 bar and the mixing was maintained at about 800 rpm. At start up, the pH was adjusted to a value of pH 6.0 with NaOH. Raney nickel (Chemcat J 10 GS) was used as a hydrogenation catalyst at a dose of 10% wet catalyst calculated on the weight of the dry substance of the batch.

Table 6 shows analyzed values before ion exchange, after ion exchange and after hydrogenation.

TABLE 6

|  | Before ion ex. | After ion ex. | After hydr. |
|---|---|---|---|
| pH | 5.9 | 5.1 | 6.9 |
| colour (Icumsa, pH 5) | 10400 | 144 | 30 |
| conductivity (microS/cm) | 6140 | 815 | 895 |
| RDS content (g/100 g) | 18.2 | 15.6 | 15.4 |
| Trehalulose (% on DS) | 5.5 | 7.3 | 2.4 |
| Isomaltulose (% on DS) | 76 | 85.5 | 0 |
| GPM (% on DS) | 0 | 0 | 44.1 |
| GPS (% on DS) | 0 | 0 | 44.4 |

RDS = Refractometric Dry Substance
GPM = α-D-glucopyranosyl-(1,1)-mannitol
GPS = α-D-glucopyranosyl-(1,6)-sorbitol
(The amount of α-glucopyranosyl-(1,1)-sorbitol was not separately measured).

EXAMPLE 7

Hydrogenation of Trehalulose

The trehalulose fraction obtained in Example 4 is subjected to hydrogenation with Raney nickel in the same manner as described in Example 6.

The hydrogenation product contains 1,1 GPM about 34% on DS, 1,6 GPS about 19% on DS and 1,1 GPS about 16% on DS.

EXAMPLE 8

Crystallization of Betaine

The betaine fractions from the chromatographic separations of Example 3 are subjected to crystallization. The dilute betaine solution containing about 55% betaine on DS is evaporated to a concentration of about 76% by weight. The resulting solution is seeded with pure betaine monohydrate crystals. Betaine monohydrate is crystallized for 4 hours at 80–85° C. under a vacuum of 130–180 mbar. The crystals are separated from the mother liquor by centrifugation, and dried.

EXAMPLE 9

Recovery of Isomaltulose and Invert Sugar

The transglucosylation of Example 2 is repeated using sugar cane molasses (Cultor Ltd.) instead of the beet molasses. The cane molasses contains 50% sucrose on DS and it is diluted to about 350 g DS/l. *P. rubrum* fermentation broth produced according to the first part of Example 2 is added to the molasses solution and the transglucosylation reaction is allowed to proceed with aeration at 30° C. until almost all of the sucrose has been converted. An anti-foaming agent (Mazu 100, PPG Industries Inc., UK) is used to control excessive foaming.

The transglucosylation product contains a major portion of isomaltulose, some trehalulose as well as invert sugar (glucose and fructose).

The transglucosylated solution is subjected to purification by filtration and ion exchange in the same manner as in Example 3. The solution is then chromatographically separated to provide separate fractions containing isomaltulose, trehalulose and invert sugar.

The isomaltulose fraction is combined with the trehalulose fraction and is hydrogenated as described in Example 6 to provide a sweetening mixture The invert sugar fraction is evaporated to provide a syrup.

The present invention has been described herein by way of some specific examples. These examples are, however, only of an illustrative nature and it is obvious to those skilled in the art that the invention may be varied in a number of ways without deviating from the scope of the appended claims.

What is claimed is:

1. A process for the simultaneous production of converted sugar products of sucrose and other sugar or non-sugar products, said process comprising the following steps:
   a) providing an aqueous sugar beet or cane derived solution containing sucrose as well as said other sugar or non-sugar products;
   b) subjecting said sucrose in said solution to transglucosylation; and
   c) recovering from said transglucosylated solution at least one of isomaltulose or trehalulose and at least one of said other sugar or non-sugar products by a process including separate chromatographical recovery.

2. The process according to claim 1, further comprising an additional step between steps a) and b), wherein said aqueous sugar beet or cane derived solution is processed in said additional step to provide molasses.

3. The process according to claim 2, wherein sucrose is recovered from said sugar beet or cane derived solution in said additional step.

4. A process according to claim 1, 3, or 2, wherein said aqueous solution is derived from sugar beets and wherein isomaltulose and betaine are recovered in step c).

5. A process according to claim 1, 3, or 2, wherein said aqueous solution is derived from sugar canes and wherein isomaltulose and invert sugar are recovered in step c).

6. The process according to claim 4, wherein said aqueous solution is derived from sugar canes and wherein isomaltulose and invert sugar are recovered in step (c).

7. A process according to any one of claims 1-3 or 2, wherein a conversion product of sucrose is recovered by crystallization.

8. A process according to claim 7, wherein said conversion product of sucrose is isomaltulose.

9. The process according to claim 1, wherein trehalulose is recovered in step c).

10. The process according to claim 1, wherein said transglucosylation is provided by sucrose glucosylmutase enzyme activity.

11. The process according to claim 10, wherein said enzyme is contained in dead or viable cells of a microorganism in free form or immobilized on a carrier.

12. The process according to claim 11, wherein said microorganism is *Protaminobacter rubrum* (CBS 574.77).

13. The process according to claim 4, wherein said betaine is recovered by ion exchange.

14. The process according to claim 4, wherein said isomaltulose is recovered by crystallization.

15. The process according to claim 1, wherein betaine is recovered by ion exchange prior to said transglucosylation.

16. The process according to claim 1, wherein said isomaltulose is hydrogenated into a mixture of α-D-glucopyranosyl-(1,1)-mannitol and α-D-glucopyranosyl-(1,6)-sorbitol.

17. The process according to claim 9, wherein said isomaltulose and/or trehalulose is hydrogenated and said hydrogenation product is recovered.

18. The process according to claim 6, wherein said fraction containing trehalulose and isomaltulose is hydrogenated to a mixture containing α-D-glucopyranosyl-(1,1)-mannitol, α-D-glucopyranosyl-(1,6)-sorbitol and α-D-glucopyranosyl-(1,1)-sorbitol.

19. The process according to claim 5, wherein a fraction containing trehalulose and isomaltulose is recovered in step c).

20. The process according to claim 4, wherein isomaltulose is recovered by crystallization.

21. The process according to claim 5, wherein isomaltulose is recovered by crystallization.

22. The process according to claim 6, wherein isomaltulose is recovered by crystallization.

23. The process according to claim 19, wherein isomaltulose is recovered by crystallization.

24. The process according to claim 19, wherein said fraction containing trehalulose and isomaltulose is hydrogenated to a mixture containing α-D-glucopyranosyl-(1,1)-mannitol, α-D-glucopyranosyl-(1,6)-sorbitol and α-D-glucopyranosyl-(1,1)-sorbitol.

* * * * *

UNITED STATES PATENT AND TRADEMARK OFFICE
CERTIFICATE OF CORRECTION

PATENT NO.      : 6,146,856
DATED           : November 14, 2000
INVENTOR(S)     : Heiki Heikkila et al.

It is certified that error appears in the above-identified patent and that said Letters Patent is hereby corrected as shown below:

Title page,
After item [22], insert the following,
-- [30]   Foreign Application Priority Data
     May 22, 1997     [FI]     Finland……..972186 --

Column 12,
Line 18, "mixture The" should read -- mixture. The --

Signed and Sealed this

Twenty-second Day of October, 2002

Attest:

JAMES E. ROGAN
Attesting Officer                    Director of the United States Patent and Trademark Office